United States Patent [19]
Jones et al.

[11] Patent Number: 5,366,601
[45] Date of Patent: * Nov. 22, 1994

[54] METHOD FOR SEPARATING IONIC SPECIES USING CAPILLARY ELECTROPHORESIS

[75] Inventors: William R. Jones, Northborough; Petr Jandik, Framingham, both of Mass.

[73] Assignee: Millipore Corporation, Bedford, Mass.

[*] Notice: The portion of the term of this patent subsequent to Apr. 14, 2009 has been disclaimed.

[21] Appl. No.: 963,685

[22] Filed: Oct. 20, 1992

Related U.S. Application Data

[63] Continuation-in-part of Ser. No. 642,685, Jan. 17, 1991, Pat. No. 5,156,724, which is a continuation-in-part of Ser. No. 471,535, Jan. 29, 1990, Pat. No. 5,104,506.

[51] Int. Cl.$^5$ .............................................. B01D 57/02
[52] U.S. Cl. .............................. 204/180.1; 250/461.1; 356/344; 356/412
[58] Field of Search .................. 204/180.1; 250/461.1; 356/344, 412

[56] References Cited

U.S. PATENT DOCUMENTS

| | | | |
|---|---|---|---|
| 4,414,842 | 11/1983 | Small et al. | 73/61.1 |
| 4,936,974 | 6/1990 | Rose et al. | 204/180.1 |
| 5,104,506 | 4/1992 | Jones et al. | 356/344 |
| 5,128,005 | 7/1992 | Jones et al. | 356/412 |
| 5,156,724 | 10/1992 | Jones et al. | 204/180.1 |

OTHER PUBLICATIONS

Burgi et al., "Capillary Electrophoresis of Anions with High Mobilities Uses Diethylene Triamine to Suppress Electro-Osmotic Flow with Sample Injected at Negative Electrode," Research Disclosure 340016, Derwent WPI, Acc. No.: 92-305906/37, Aug. 10, 1992.
X. Huang et al., "Quantitative Analysis of Low Molecular Weight Carboxylic Acids by Capillary Zone Electrophoresis/Conductive Detection", *Anal. Chem.*, 61: 766–770 (1989).
F. Foret et al., "Indirect Photometric Detection in Capillary Zone Electrophoresis", *J. Chromatography*, 470: 299–308 (1989).
W. G. Kuhr and E. S. Yeung, "Optimization of Sensitivity and Separation in Capillary Zone Electrophoresis with Indirect Fluorescence Detection", *Anal. Chem.*, 60: 2642–2646 Dec. 1988.
W. G. Kuhr and E. S. Yeung, "Indirect Fluorescence Detection of Native Amino Acids in Capillary Zone Electrophoresis", *Anal. Chem.*, 60: 1832–1834 (1988).
T. Takeuchi et al., "Indirect Fluorometric Detection in Micro High-Performance Liquid Chromatography", *Chromatographia*, 25: 1072–1074 Dec. 1988.
K. D. Altria and C. F. Simpson, "High Voltage Capillary Zone Electrophoresis: Operating Parameters Effects on Electroendosmotic Flows and Electrophoretic Mobilities", *Chromatographia*, 24: 527–532 (1987).
T. Tsuda et al., "Separation of Organic and Metal Ions by High-Voltage Capillary Electrophoresis", *J. Chromatography*, 264: 385–392 (1983).
J. W. Jorgenson and K. D. Lukacs, "Capillary Zone Electrophoresis", *Science*, 222: 266–272 Oct. 1983.
F. Foret et al., "On-Line Fiber Optic UV Detection Cell and Conductivity Cell for Capillary Zone Electrophoresis", *Electrophoresis*, 7: 430–432 (1986).
A. Nardi et al., "Capillary Zone Electrophoretic Separation of Cyclodextrins with Indirect UV Photometric Detection", *Electrophoresis*, 11: 774–776 (1990).
F. Foret et al., "Capillary Zone Electrophoresis of Rare Earth Metals with Indirect UV Absorbance Detection", *Electrophoresis*, 11: 780–783 (1990).

*Primary Examiner*—John Niebling
*Assistant Examiner*—C. Delacroix-Muirheid
*Attorney, Agent, or Firm*—Hamilton, Brook, Smith & Reynolds

[57] ABSTRACT

A technique for separating, identifying and measuring ions in solution by capillary zone electrophoresis is described, which provides improved sensitivity and resolution of anionic species. The method involves introducing a sample containing the ionic species into a narrow bore capillary filled with a carrier electrolyte containing a selected light-absorbing anion. An electrical potential is applied across the capillary column causing the ions to elute according to their ionic mobility. Both UV absorbing and UV-transparent ions can be detected and quantitated by UV/visible photometric monitoring.

13 Claims, 15 Drawing Sheets

METHOD FOR SEPARATING IONIC SPECIES USING CAPILLARY ELECTROPHORESIS

RELATED APPLICATIONS

This application is a continuation-in-part of U.S. application Ser. No. 07/642,685, filed Jan. 17, 1991, now U.S. Pat. No. 5,156,724 which is a continuation-in-part of U.S. Ser. No. 07/471,535, filed Jan. 29, 1990, now U.S. Pat. No. 5,104,506.

BACKGROUND

The separation and/or detection of ionic species is generally carried out by utilizing electrochemical properties of analytes, such as ionic interactions and conductivity in ion chromatography or ionic mobility in capillary electrophoresis. Ion chromatography (IC) is capable of detecting simultaneously a large variety of ionic species at low concentration levels. The ability to separate and detect several widely different ionic species simultaneously is a unique characteristic of IC. In fact, the commercial viability of IC depends in part on its ability to simultaneously separate and detect, inter alia, seven common inorganic anions ($F^-$, $Cl^-$, $NO_2^-$, $Br^-$, $NO_3^-$, $HPO_4^{2-}$ and $SO_4^{2-}$). However, there are important limitations to IC, including lack of sufficient selectivity for certain types of mixtures, low separation efficiency and a relative complexity of instrumentation.

Capillary electrophoresis (CE) is an efficient analytical separation technique for analysis of minute amounts of sample. CE separations are performed in a narrow diameter capillary tube, which is filled with an amounts of sample. CE separations are performed in a narrow diameter capillary tube, which is filled with an electrically conductive medium termed the "carrier electrolyte". A potential is applied to the carrier electrolyte, and ionic species in the sample move from one electrode toward the other at a rate which is dependent upon certain characteristics, such as molecular charge, size and/or mobility. CE may be performed using gels or liquids, such as buffers, in the capillary. In the liquid mode, known as free zone electrophoresis, separations are based on the ratio of charge to Stoke's radius.

CE has several advantages over IC for the separation of ionic species. These include improved resolution and smaller sample size. In part, high resolution can be obtained since band broadening is minimized due to suppressing diffusional processes to a major extent. In free-zone electrophoresis, the phenomenon of electroosmosis, or electroosmotic flow (EOF), which is the bulk flow of liquid, rapidly moves all of the sample molecules whether they are positively charged, negatively charged or neutral. Under certain conditions EOF can contribute to improved separation speed in free-zone CE.

The detection of ionic species by CE is problematical particularly if all seven of the common anions mentioned above are to be determined simultaneously. Most ions do not absorb light, so they cannot be detected by conventional photometric means, e.g., direct photometric or fluorescent detection. However, these ions can be detected using indirect photometric detection. Indirect photometric detection relies upon the presence of a light absorbing electrolyte ion in the background electrolyte. Non-absorbing species are detected as zones of decreased absorbance or voids in the background due to the displacement of the light absorbing electrolyte ion. Indirect photometric detection has been described using fluorescent, ultraviolet (UV) and UV-visible (UV-vis) absorbing ions in the background electrolyte. For example, Small et al. in U.S. Pat. No. 4,414,842 describe a technique for detecting ions in an ion exchange chromatography system by indirect UV detection in which a UV-absorbing ion is included in the elution buffer. Methods utilizing indirect photometric detection in capillary electrophoresis have been described by Foret et al., *J. Chromatography*, 470: 299–308 (1989); Kuhr et al., *Anal. Chem.*, 60: 2642–2646 (1988); Kuhr et al., *Anal. Chem.*, 60: 1832–1834. However, these and other methods have not proved satisfactory. For example, none of these methods were able to separate and detect a mixture of eight standard anions ($Br^-$, $Cl^-$, $SO_4^{2-}$, $NO_2^-$, $NO_3^-$, $F^-$, $HPO_4^{2-}$ and $CO_3^{2-}$). The main reason is the inability of previously reported indirect photometric methods to provide the same level of sensitivity for transparent ions (e.g., $F^-$, $Cl^-$, $SO_4^{2-}$) and UV-absorbing ions (e.g., $NO_2^-$, $NO_3^-$). All published CE methods have failed to successfully separate ions of widely differing properties, e.g., slow migrators such as $F^-$, $PO_4^{3-}$ and fast migrators such as $Br^-$, $SO_4^{2-}$. The need exists for a method for separating and detecting these and other ionic molecules which is faster, more efficient, has better resolution, and requires less sample preparation than the available methods.

SUMMARY OF THE INVENTION

The present invention relates to methods for separating and detecting anions by CE using carrier electrolyte solutions which facilitate detection by indirect methods, particularly UV/visible spectroscopy. The present methods rely upon reagents which can simultaneously effect a sensitive, high resolution separation of several widely different ionic species, ranging from simple inorganic ions to complex organic ions, and both slowly migrating and quickly migrating ions.

The methods generally involve introducing a sample containing the ions into a CE system which utilizes reagents which provide a light-absorbing background at a wavelength suitable for sensitive and interference-free indirect photometric detection of all ionic species without regard to their respective intrinsic UV absorption properties.

The sample is injected into a capillary filled with the carrier electrolyte containing the reagent mixture, an electric potential is applied to the capillary under conditions appropriate to cause the ions in the mixture to move toward the electrode at the opposite end of the capillary and the ionic species are detected photometrically.

The reagent mixture which is most effective as a component in a carrier electrolyte for separating anions consists of the salt of a UV-absorbing anion (e.g., bromide, iodide, tungstate, molybdate, chromate, dichromate, ferrocyanide, ferricyanide or vanadate). Chromate and vanadate compounds are often the preferred reagents for most anion separations, in part because of their ionic mobilities relative to the common inorganic anions and because of their unusually broad UV spectra, but the other listed UV-absorbing anions are equally effective as detection species. In addition, one or more reagents for controlling the speed and/or direction of the electroosmotic flow of the carrier electrolyte can, optionally, be included in the electrolyte mixture. Examples of such reagents include surfactant substances, polymeric materials and organic salts. These reagents can exist as free substances in the reagent mixture or as materials bound by chemical or absorptive forces to the capillary wall. Alternatively, the electroosmotic flow can be increased by raising the pH, thus increasing the observed migration rates of anions. The observed migration rates of anions can be decreased by reducing the pH of the reagent mixture solution to a value of about pH 4 or lower. The electroosmotic flow can be reversed by using a suitable additive. These electroosmotic flow alterations which affect the observed migration rates of the anions occur by altering the electrical charge on the inner surface of the capillary material. The surfactant, polymer or organic salt substances are examples of additives which are electroosmotic flow moidifiers and can be included in the reagent mixture when the mixture is at these increased or decreased pH values.

In addition to the UV-absorbing anion and the flow modifier, an electromigrative agent can be added to the system. The electromigrative agent which enhances the detection of trace anions, e.g., species present in nanomole concentrations, is generally added to the sample containing the analyte ions.

The chemistry necessary to perform CE separations of ionic species for indirect detection can be contained in a kit. Such a kit for separating anions would contain, inter alia, one or more light absorbing ions specific for the UV/visible range, and, optionally, one or more reagents for controlling the speed and/or the direction of the electroosmotic flow of the carrier electrolyte.

The present reagent compositions and methods have several advantages, such as improved sensitivity, linearity of the range of calibration, the ability to separate and resolve a wide range of anionic species, the ability to detect ionic species which are not detectable by direct methods in addition to ions that are detectable by direct methods, less sample preparation and faster separation. The methods can be used to separate and detect both simple and complex anions and to detect a variety of analytes simultaneously.

DETAILED DESCRIPTION OF THE INVENTION

Figure 1:
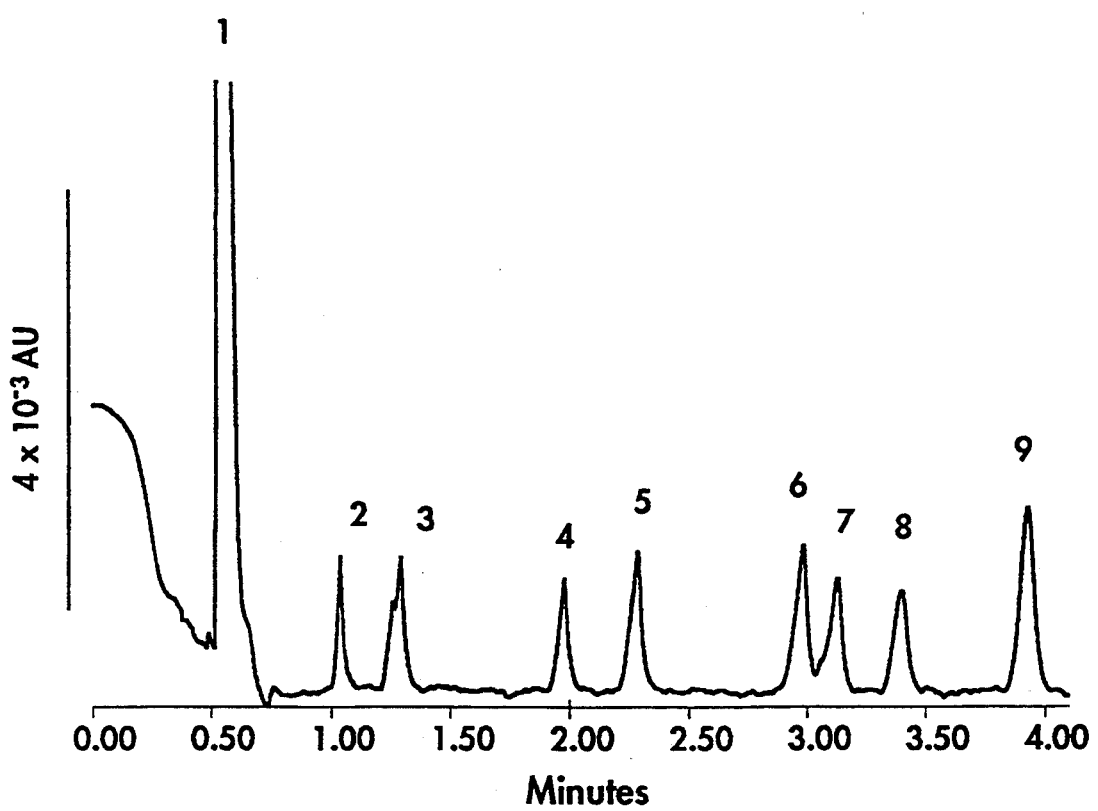
FIG. 1 is an electropherogram showing the separation of eight anions, including persulfate, by CE using chromate as the detection anion in a pH 11 carrier electrolyte solution.

The present method utilizes CE to simultaneously separate and detect ionic species having widely different properties contained in a sample using indirect UV/visible detection. Indirect UV/visible spectroscopy is used because many ionic species cannot be detected using direct detection methods. CE is a well known technology, and has been described in detail, for example, by Compton and Brownlee in *Biotechniques*, 6(5): 432–440 (1988); and Jorgenson and Lukacs in *Science*, 222: 266–272 (1983). A method of utilizing indirect photometric detection in CE is described by Foret et al. in *J. Chromatography*, 470: 299–308 (1989).

The present method is generally carried out using the following procedure: a capillary tube is filled with an electrically conductive liquid (the carrier electrolyte) containing one or more reagents which facilitate detection by UV/visible spectroscopy. A preferred capillary is generally a fused silica capillary having an internal diameter of from about 50 to 100 microns ($\mu$).

The ionic sample is introduced into the capillary, for example, by hydrostatic pressure, vacuum or by electromigrative injection in which components from the liquid sample are moved into the capillary by an electric current. After introduction of the sample, each end of the capillary is immersed in a reservoir which contains an electrode and the carrier electrolyte solution containing the reagents. The capillary tube is positioned with a detector on the column near the end opposite to sample introduction. Electric current is applied causing the anions to move along the capillary toward the detector. The ions move at different speeds, depending upon several factors, such as their size and mobility. The electrophoretic separation is preferably monitored by indirect UV/visible spectroscopy. Other indirect detection methods can be used; however, UV/visible spectroscopy is preferred because it allows sensitive rapid detection of ionic species and is less costly than laser enhanced fluorescence detection, for example.

The method relies upon reagents which facilitate detection by indirect UV/visible spectroscopy, comprising light-absorbing compounds specific for the UV/visible range. For detecting anions, a UV-absorbing anion is used in the carrier electrolyte.

UV/visible light-absorbing compounds which are useful for separating and detecting anions are UV-absorbing anions, such as bromide, iodide, tungstate, molybdate, chromate, dichromate, ferrocyanide, ferricyanide and vanadate salts. The absorbing anions (detection anions) are usually present in the capillary reagent solution in a concentration of from about 1 mM to about 20 mM. Particularly preferred concentrations of the absorbing anions are from about 2 mM to about 5 mM.

The carrier electrolyte can also contain, in addition to the UV-absorbing anion, a flow modifier, which is a compound which slows, stops or reverses the electroosmotic flow of the carrier electrolyte. Electroosmotic flow is the bulk flow of the electrolyte through a capillary that is induced by an applied electric field. The amount of flow and its direction is dependent, in part, on the charge of the inner wall of the capillary. If there is no wall charge, there is no electroosmotic flow. Thus, flow modifiers can eliminate or reverse the effects of the capillary wall on the flow of the electrolyte. Negating or counteracting the wall effects can improve the resolution of the desired analyte ions. Flow modifiers which are useful in the present method include surfactants, polymeric materials and organic salts. Surfactants which are useful include, e.g., alkyl amines, such as diaminononane and di-n-butylamine, and commercially available surfactants such as Tween 20. Polymeric materials that are useful in the methods of the present invention include such substances as polyethylene glycol, polymethylsiloxane and polybutadiene maleic acid copolymers. Organic salts that can be used in the methods include cationic surface active agents, such as alkyl ammonium, arsonium and phosphonium compounds containing at least eight carbon atoms in a linear or branched configuration. Such compounds include for example, quaternary ammonium salts, arsonium salts and phosphonium salts, biammonium salts, biphosphonium salts and biarsonium salts. These compounds include, for example, octyl trimethylammonium, phosphonium or arsonium, various alkyl derivatives of 1,8-diaminooctane, 1,8-diphosphinooctane or 1,8-diarsinooctane. Compounds which are particularly useful are quaternary ammonium salts which contain alkyl groups having at least eight carbon atoms in a linear or branched configuration. Preferred quaternary ammonium salts are tetradecyltrimethylammonium bromide (TTAB) and/or cetyltrimethylammonium bromide (CTAB). A concentration of TTAB or CTAB of from about 0.1 mM to about 5.0 mM is useful in the present method. Also suitable are some polymeric ammonium, phosphonium and arsonium salts, such as, for example, hexadimethine bromide. Amphoteric ammonium compounds, such as, for example, 3-N-N-dimethylpalmitylammonia propanesulfonate are also useful flow modifiers.

The use of flow modifiers facilitates control of both the direction, as well as the rate of electroosmotic flow. Control of this parameter permits the development of an assay that is both high in resolution and is complete in a short period of time. The carrier electrolyte solution generally has a pH of from about 7.5 to about 8.5. However, the carrier electrolyte solution pH can be adjusted downward or upward in order to change the electroosmotic flow by creating an altered surface charge on the capillary glass. Increasing the solution pH to a value of about pH 11 or above often results in an increase of the electroosmotic flow toward the cathode (normal direction of the electroosmotic flow). As a consequence, the observed migration rates of anions are also increased (sampling site positive, no reversal of electroosmotic flow). Decreasing the carrier electrolyte solution pH to a value below pH 4 slows the electroosmotic flow and can, in some instances (pH less than 3), result in a reversal of the electroosmotic flow (reverse electroosmotic flow). An acid, or its salt, such as sulfuric acid or sulfate, or, alternatively, chromic acid or chromate, can be added to the electrolyte solution to adjust the pH to the desired level.

In another embodiment of the present method, various aromatic carboxylic acids can be used as components in carrier electrolytes. The main usefulness of carboxylates as carrier electrolytes is in the CE analysis of less mobile anions (e.g., fluoride, carboxylic acids, alkylsulfonates), which may produce broadly asymmetric peaks if analyzed using the chromate electrolyte. However, because of their relatively low mobilities, aromatic carboxylates are less suitable than chromates as electrolytes for analysis of complex mixtures of highly mobile inorganic anions. The best results are obtained in CE when the mobilities between the main anionic components of the carrier electrolyte and the analyte ions is closely matched. Therefore, a range of highly UV-absorbing carrier electrolytes covering the range of ionic mobilities of all inorganic anions and other low molecular weight species is of practical interest. Aromatic carboxylates are useful in the present method for detecting and measuring some organic anionic species having low ionic mobility and which are UV-transparent, such as carboxylic acids, amino acids, carbohydrates or sulfonates. Aromatic carboxylates such as phthalate, trimesate, benzenetetracarboxylate, p-hydroxybenzoate, and p-anisate are useful for this purpose.

In another embodiment of the present composition and method for separating and detecting anions, an electromigrative agent can be added to the sample in order to enhance the separation and/or detection of trace amounts of anions, e.g. nanomolar quantities. The addition of an electromigrative agent to the sample provides enrichment of the separation of anions present in the sample in concentrations in the nanomolar range. In this embodiment, the agent is added to the sample, and the sample is injected into the capillary using electromigrative sample introduction. Electromigrative sample introduction involves applying a current having very low amperage which selectively causes the trace anions to migrate toward the capillary. The addition to the sample of the electromigrative agent, which has a lower ionic mobility in comparison to the carrier electrolyte anion, results in the selective migration of the trace anions into the capillary, which effectively preconcentrates these anions, thereby enriching the sample to be analyzed with the trace anions. In addition to the analyte anions, it is also possible to observe the enrichment of sample matrix anions acting as an isotachophoretic terminating electrolyte. Such anions may be added purposely. In solutions containing total ionic concentrations in the nanomolar range, sample conductivity often becomes too low, and can be adjusted by a suitable additive to enable sufficient electric charge throughput for ionic transfer from the bulk of the sample solution into the capillary. For this purpose, citrate, carbonate and octanesulfonate salts can be used as electromigration additives.

Citrate, carbonate and octanesulfonate salts which exhibit lower ionic mobilities in comparison with the UV-absorbing anion in the carrier electrolyte (e.g., chromate) can be used as additives for electromigrative trace enrichment with the UV-absorbing anions in the carrier electrolyte. Sodium octanesulfonate adjusted within the range of 15 to 70 $\mu M$ is particularly useful electromigration agent in low ionic content samples. Addition of relatively excessive concentrations of octanesulfonate does not lead to interfering comigration with any of over fifty anionic species analyzed by the present CE method. Sodium octanesulfonate can be obtained free of common ionic impurities which could disturb the quantitation of common anions such as sulfate and chloride in unknown samples. The detection limits (calculated as noise times three in concentration units) for this separation are in the low nanomolar range. This represents at least a hundredfold increase in sensitivity in comparison with the results achievable in the same carrier electrolyte and with hydrodynamic sample introduction.

The present methods can be utilized to analyze most types of ionic species. Samples containing complex mixtures of ions, including anions, cations and organic compounds, for example, can be analyzed using the method. When a sample containing such a complex mixture is separated using the present methods and electrolyte carriers for separating anions, for example, the detector is placed just before the anode immersed in an electrolyte and the cathode is placed in another portion of the same electrolyte at the opposite end when reverse direction of the electroosmotic flow is employed. Thus, the cations in the sample will move away from the detector, and the organic species will move very slowly toward the anode, thereby creating a window for the anionic species toward the detector. The anions move most rapidly toward the detector, thus are most efficiently resolved. When reverse electroosmotic flow is employed, the polarity of the electrodes is reversed and the anions are carried toward the cathode. The detector is placed just before the cathode, in this situation, and the sample may be injected at the anode end of the capillary.

The present methods are useful for analyzing samples containing multiple ionic species in the shortest time possible, or to scan an unknown sample for ionic compounds, since the methods and reagent mixtures can efficiently separate and resolve such mixtures. Samples which can be analyzed using the present methods include water, foods, such as juices, biological fluids or industrial chemical mixtures.

In one embodiment of the present method, a sample containing eight common inorganic anions: bromide, chloride, nitrate, nitrite, sulfate, fluoride, phosphate and carbonate, was analyzed by CE using a mixture of 0.5 mM TTAB and 5 mM sodium chromate ($Na_2CrO_4$) having a pH of 8 as the carrier electrolyte. All eight anions were detected by monitoring the absorbance of the carrier electrolyte at 254 or 272 nm. Separation of all eight anions was completed in about three minutes. The ionic species were separated based on their ionic mobilities. This is important because the migration sequence using the present method is predictable based on the known ion mobilities of various ions. This means that the chemical identity of an unknown analyte can be reliably determined from its position in the migration order.

Separation of ionic species using the present compositions and methods is superior to ion chromatographic separations of similar mixtures in several respects: improved separation efficiency, shorter runtime, better selectivity, linearity of the plot and improved sensitivity. For example, the number of theoretical plates for sulfate in the illustrative example used above is 157,344. The highest plate-counts attainable by ion chromatography are less than 10,000. Separation of the standard eight anions was completed in three minutes by the present method, whereas ion chromatographic separations of identical mixtures take typically six to fifteen minutes. Injection volumes for the CE separation are less than about 40 nanoliters (nl) compared to about 50 to 100 microliters ($\mu l$) for IC. Even though only 20 nL were injected to obtain the above separation, detection limits for all separated anions were either comparable or better than those observed in IC. This corresponds to a 10,000 fold increase in absolute sensitivity (per $\mu g$ injected) in the present CE system in comparison with IC.

The present methods provide ionic separations which are efficient, highly selective, and which have a predictable order of elution. The methods exhibit increased selectivity for ionic separations as compared to other methods such as IC. During a typical CE separation of anions using a reagent mixture which includes the detection anion, cationic compounds usually migrate in the opposite direction away from the anions of interest and are not seen in the electropherogram. Neutral and slightly polar impurities are considerably less mobile than the anions and have longer migration times. Thus, the anions of interest are efficiently separated and resolved in the shortest time.

The practical usefulness of such increased selectivity can be illustrated, for example, using a fruit juice as the sample. When orange juice is directly injected into an IC system, the first five peaks to elute, which represent fluoride, chloride, nitrite, bromide and nitrate ions, are subjected to interference by carboxylic acids, such as formate or acetate and other organic compounds in the sample. To reduce this interference, analysis of the anions in the juice using IC would require a complicated pretreatment of the sample to remove the carboxylates and organic compounds. The same sample can be successfully analyzed by CE, and good separation of the anions can be obtained without any pretreatment of the sample using the present method.

The invention is further illustrated by the following Examples.

EXAMPLE 1

General Procedure For CZE of Anions Using $Na_2CrO_4$/TTAB Electrolyte

A sample containing the following eight inorganic anions was prepared: fluoride (F), carbonate ($CO_3$), chloride (Cl), nitrite (NO2), nitrate (NO3), bromide (Br), phosphate (PO4) and sulfate (SO4).

A fused silica capillary externally coated with polyimide (Polymicro Technologies) was freshly cut from a roll and approximately a 1 cm section of polyimide coating was burned off with a butane lighter for UV light to pass through at 40.5 cm from one end. The total capillary length was 63 cm, and had an internal diameter of 75 μm. The capillary was installed into the photometric cell and purged with electrolyte with a 1 cc luer syringe with an adapter. The electrolyte was 5M Na2CrO4 and 0.5 mM TTAB, adjusted to pH 8 with 10 mN sulfuric acid. A 50 ml beaker and a 100 ml beaker were filled with electrolyte to equal heights. The 50 ml beaker was placed at the cathode end of the capillary and the 100 ml was placed at the anode end. Approximately 100 microliters of carrier electrolyte was run through the capillary prior to analysis.

The power supply (Spellman (0 to 30 KV)) was manually turned to zero. The capillary at the cathode end was picked up manually, raised to 16 cm height above the electrolyte level and placed in the sample for 30 seconds. The capillary was removed from the sample and placed promptly into the electrolyte. The voltage was manually ramped from 0 to 20 KV during approximately 10 seconds while the start integrate signal was initiated at the beginning of the voltage ramp. At 20 RV a typical current reading was about 20 μA.

Detection was carried out using a Linear Instruments variable UV/Vis CE detector at two different wavelengths: 254 nm and 272 nm.

Separation was completed in about three minutes, and a clear and distinct peak was obtained for each anion. All eight anions were separated within about one minute.

EXAMPLE 2

CE Separation of a Complex Mixture of Anions

The separation of a complex mixture of ten (10) weakly and strongly dissociated anionic species was carried out according to the procedure described in Example 1. The ten anions in the mixture were: Cl, S4, NO3, F, CO3, formate, acetate, propionate, butyrate and an unidentified organic acid. Separation was completed within about 3.8 minutes. All ten anions migrated through the photometric cell and were detected, and a clear and distinct peak was obtained for each anion.

EXAMPLE 3

CE Separation of a Complex Mixture of Eight Anions Including Persulfate

The separation of a mixture of eight anions and one neutral species was carried out according to the general procedure described in Example 1, except that the polarity of the sampling end was reversed and the flow modifier TTAB was not used. One of the eight anions was persulfate. The detection anion was 5 mM chromate in an electrolyte solution titrated to pH 11 with lithium hydroxide and indirect UV/visible detection was carried out at 254 nm. The nine species were:

|   | Anion | ppm |
|---|---|---|
| 1. | neutral species | — |
| 2. | fluoride | 1 |
| 3. | carbonate | — |
| 4. | nitrate | 4 |
| 5. | nitrite | 4 |
| 6. | sulfate | 4 |

-continued

|   | Anion | ppm |
|---|---|---|
| 7. | chloride | 2 |
| 8. | bromide | 4 |
| 9. | persulfate | 10 |

Separation of these substances was completed in less than four minutes. All nine peaks were detected and a clear and distinct peak was obtained for each species including persulfate, as shown in FIG. 1. The numbers on the peaks correspond to the numbers in the above list.

EXAMPLE 4

CE Separation of Seven Anions Using Di-n-Butylamine as the Electroosmotic Flow Slow Down Reagent The separation of a mixture of seven anions was carried out according to the procedure set out in Example 3, except that di-n-butylamine was used as a modifier. The pH of the electrolyte solution containing 5 mM chromate and 130 μL of di-n-butylamine in 500 mL of the electrolyte solution was pH 10.6. Indirect UV/visible detection was carried out at 272 nm.

Figure 2:
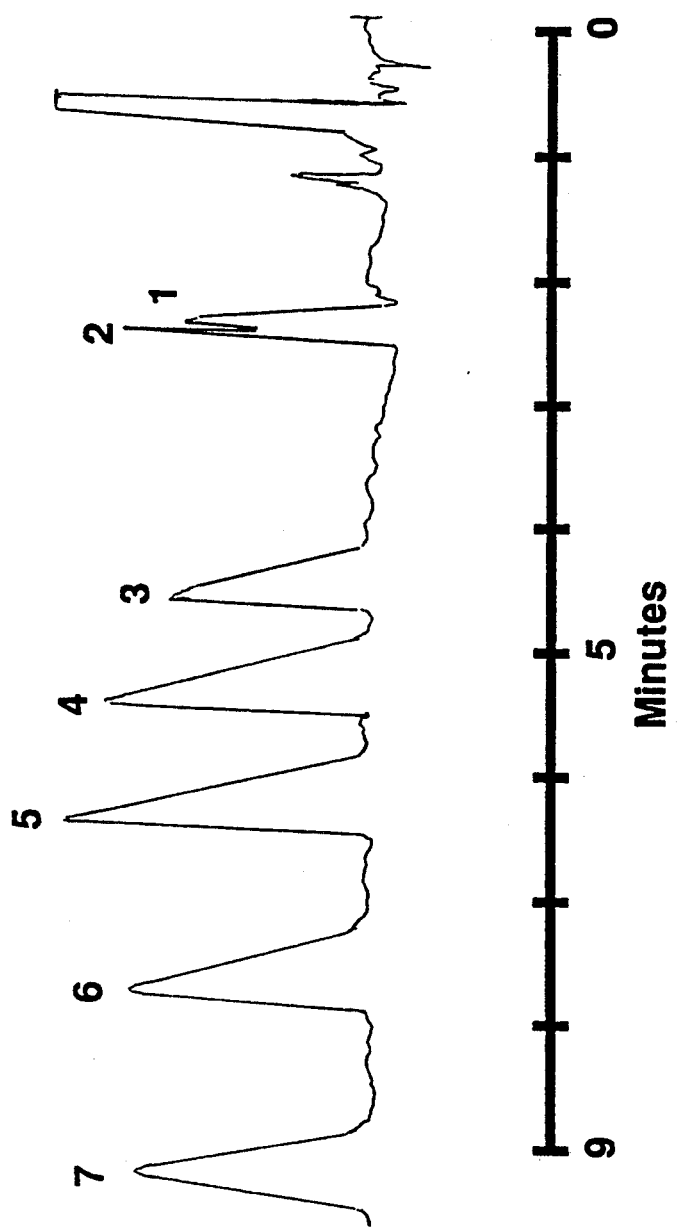
FIG. 2 is an electropherogram showing the separation of seven anions by CE using chromate as the detection anion and di-n-butylamine as the modifying reagent which slows the electroosmotic flow.

The seven anions were separated by the procedure in less than ten minutes, as shown in FIG. 2.

The seven anions shown in FIG. 2 are:
1. fluoride
2. phosphate
3. nitrite
4. nitrate
5. sulfate
6. chloride
7. bromide

EXAMPLE 5

CE Separation of a Mixture of Seven Anions using Iodide as the Detection Anion

The separation of the mixture of anions as in Example 4 was carried out according to the general procedure and conditions described in that Example, except that 5 mM iodide as the potassium salt was the detection anion rather than chromate. Di-n-butylamine was the electroosmotic flow modifying reagent. Indirect UV/visible detection was carried out at 234 nm.

Figure 3:
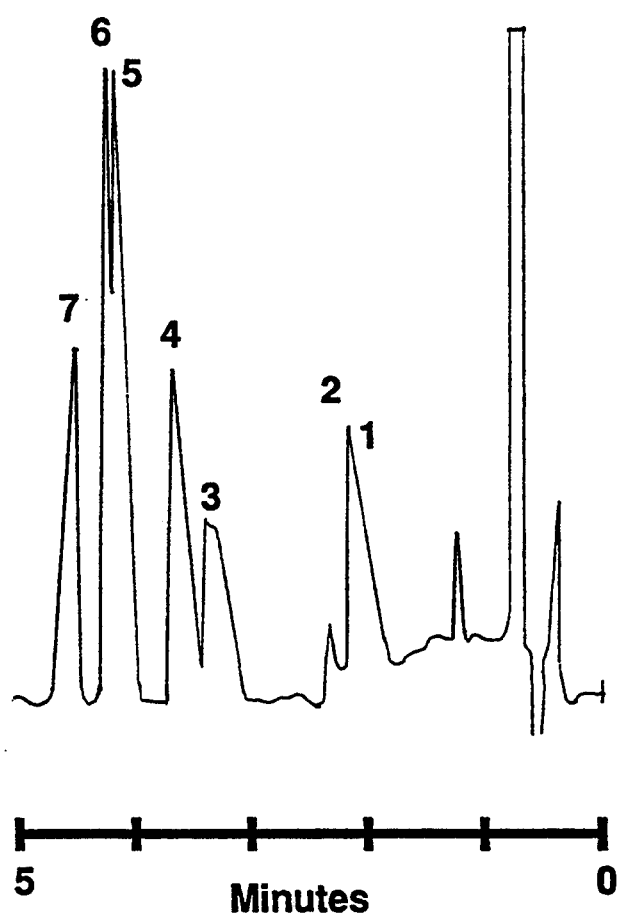
FIG. 3 is an electropherogram showing the separation of anions by CE using iodide as the detection anion and di-n-butylamine as the modifying reagent which slows the electroosmotic flow.

The anions were separated and detected by the procedure in less than five minutes as shown in FIG. 3. The peak identities were the same as in Example 4.

EXAMPLE 6

CE for Anions Using Dichromate as the Detection Anion

A capillary electrophoresis separation procedure was carried out according to the general procedure and conditions of Example 3 with the following exceptions. The detection anion was 2 mM dichromate in an electrolyte solution at pH 2.93. The power supply was oriented so that the detection of the anion accurred at the anode end of the capillary. Indirect UV/visible detection was carried out at 387 nm.

Figure 4:
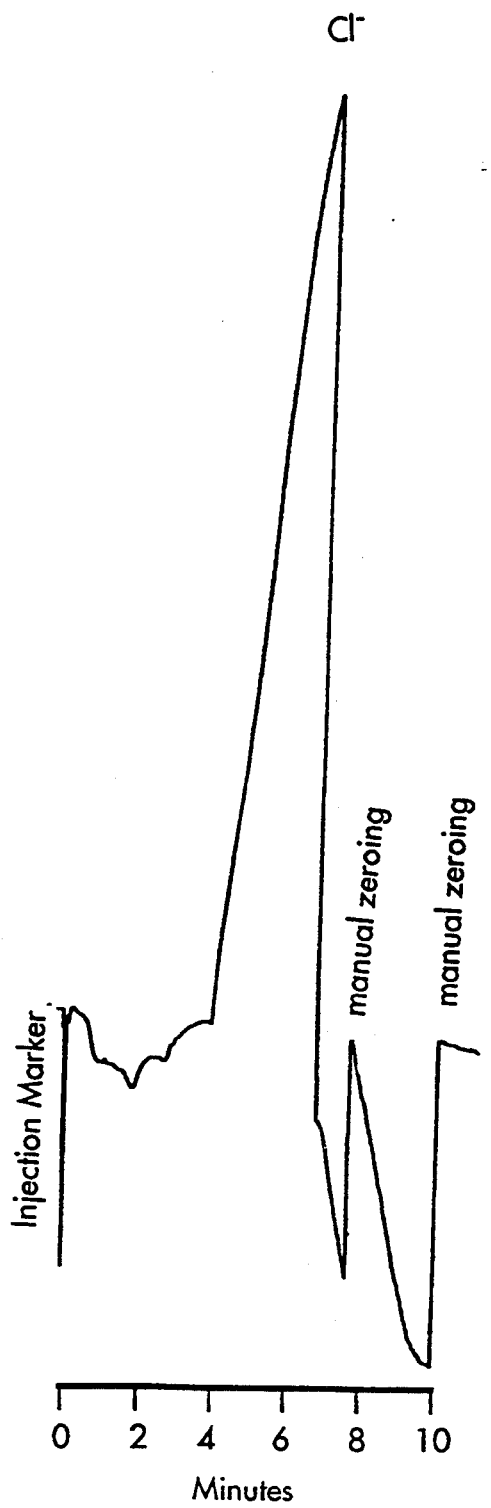
FIG. 4 is an electropherogram obtained by slowing down the electroosmotic flow and shows detection of the chloride anion by CE using dichromate as the detection anion.

As can be seen from FIG. 4, chloride was detected by the procedure of this Example.

EXAMPLE 7

CE Separation of a Mixture of Six Anions by Reverse Electroosmotic Flow

The separation of a mixture of six anions was carried out according to the general procedure and conditions described in Example 1 with the following exceptions. The detection anion was 5 mM molybdate as the sodium salt. The power supply was reversed so that detection of the anions occurred at the anode end of the capillary (reverse electroosmotic flow). The electroosmotic flow reversing reagent remained as TTAB.

Figure 5:
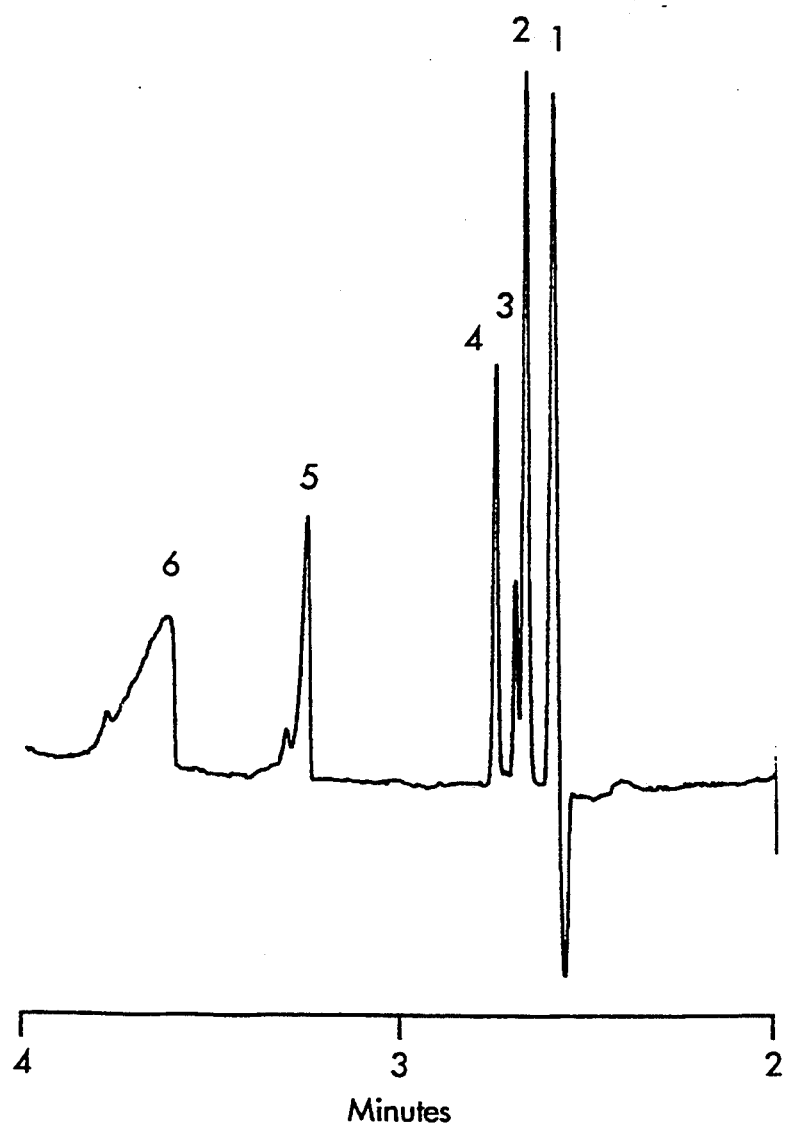
FIG. 5 is an electropherogram obtained by reverse electroosmotic flow showing the separation of five anions by CE using molybdate as the detection anion and tetradecyltrimethylammonium bromide (TTAB) as the electroosmotic flow reversing reagent.

The six anions were separated and detected by the procedure as shown in FIG. 5.

The six anions shown in FIG. 5 are:

|   | anion | ppm |
|---|---|---|
| 1. | chloride | 2 |
| 2. | sulfate | 4 |
| 3. | nitrite | 4 |
| 4. | nitrate | 4 |
| 5. | fluoride | 1 |
| 6. | phosphate | 4 |

EXAMPLE 8

CE Separation of a Mixture of Eight Anions by Reverse Electroosmotic Flow Using Ferrocyanide as the Detection Anion The separation of a mixture of eight anions by reverse electroosmotic flow was carried out according to the general procedure and conditions described in Example 7, except that 5 mM ferrocyanide as the potassium salt was the detection anion rather than molybdate. The electroosmotic flow modifying reagent was 0.1 mM TTAB. Indirect UV/visible detection was carried out at 425 nm.

Figure 6:
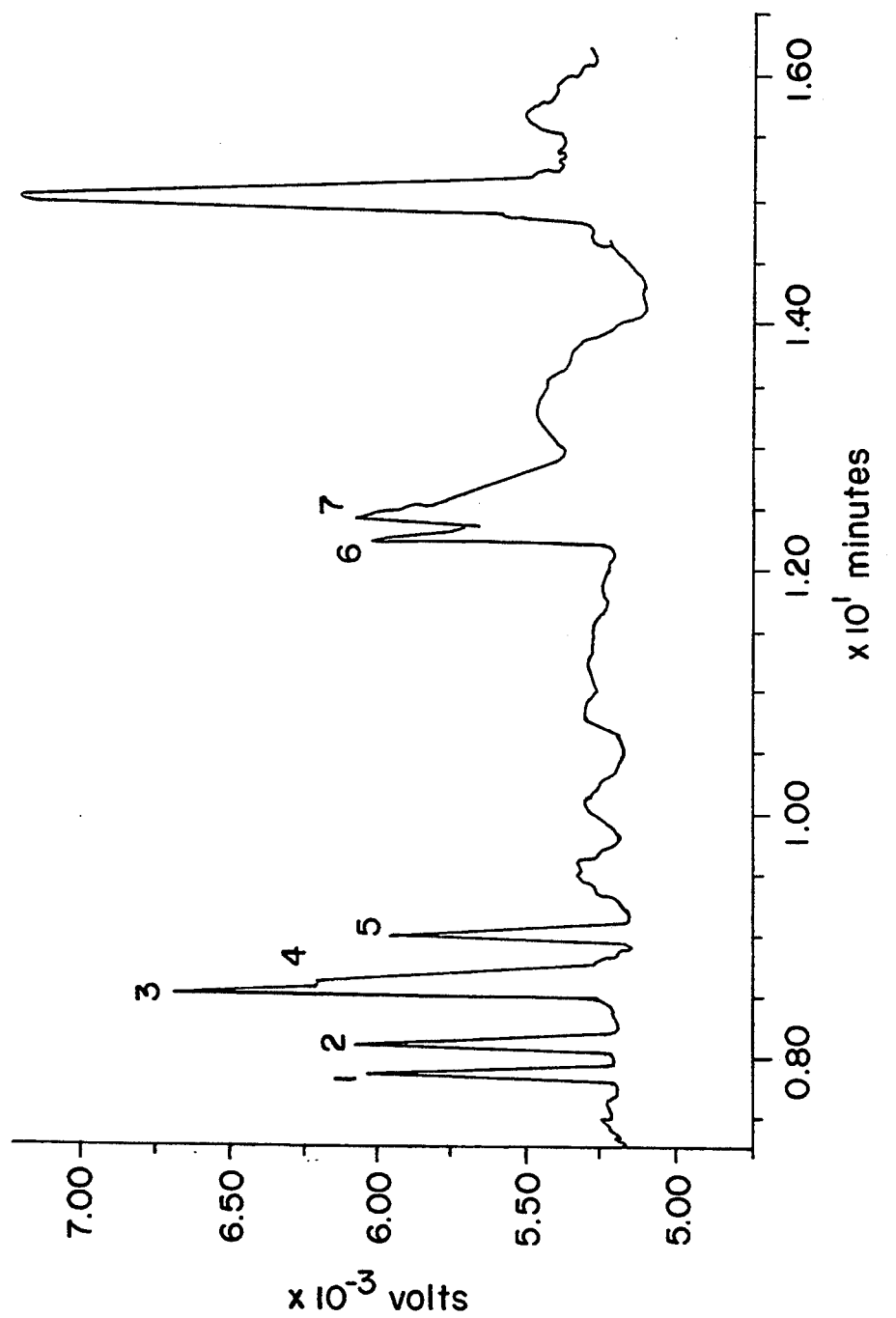
FIG. 6 is an electropherogram obtained by reverse electroosmotic flow showing separation of anions by CE using ferrocyanide as the detection anion and TTAB as the electroosmotic flow reversing reagent.

The eight anions were separated and detected by the procedure as shown in FIG. 6.

The eight anions shown in FIG. 6 are:

| 1. | fluoride |
|---|---|
| 2. | phosphate |
| 3. | nitrite |
| 4. | nitrate |
| 5. | sulfate |
| 6. | chloride |
| 7. | bromide |
| unlabeled peak | carbonate |

EXAMPLE 9

CE Separation of a Mixture of Anions by Slowed Down Electroosmotic Flow Using Diaminononane as the Electroosmotic Flow Modifying Reagent The separation of a mixture of anions by slowed down electroosmotic flow was carried out according to the following general procedure and conditions. The detection anion was chromate and the electroosmotic flow modifying reagent was 0.5 mM 1,9-diaminononane. The polarity of the end of the capillary in which the sample was injected was negative. Indirect UV/visible detection was carried out at 254 nm.

Figure 7:
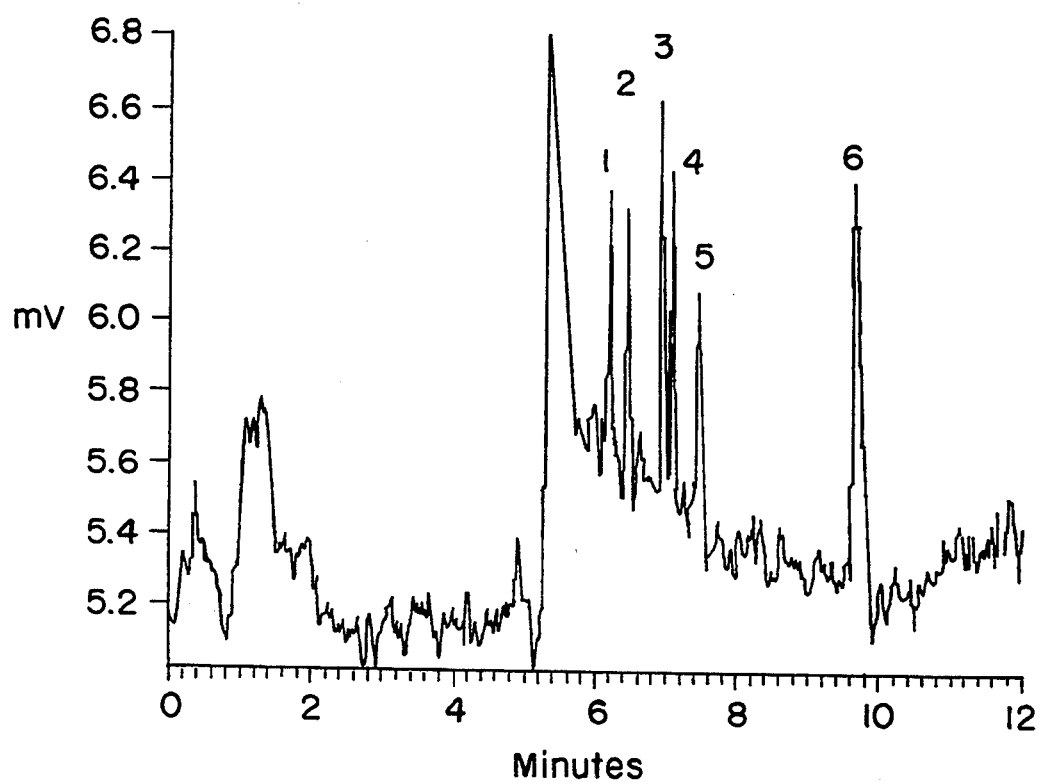
FIG. 7 is an electropherogram obtained by reverse electroosmotic flow showing separation of anions by CE using chromate as the detection anion and diaminononane as the electroosmotic flow modifying reagent.

The anions were separated and detected by the procedure in less than ten minutes, as shown in FIG. 7.

The separated anions shown in FIG. 7 are:

|   | anion | ppm |
|---|---|---|
| 1. | bromide | 4 |
| 2. | chloride | 2 |
| 3. | sulfate | 4 |
| 4. | nitrite | 4 |
| 5. | nitrate | 4 |
| 6. | fluoride | 1 |

-continued

| anion | ppm |
|---|---|
| and phosphate | 4 |

EXAMPLE 10

CE Separation of a Mixture of Five Anions by Slowed Down Electroosmotic Flow Using 3-N,N-Dimethylpalmitylammonia Propanesulfonate as the Electroosmotic Flow Modifying Reagent The separation of a mixture of five anions by slowed down electroosmotic flow was carried out according to the general procedure and conditions described in Example 9, except that 3-N,N-dimethylpalmitylammonia propanesulfonate was the electroosmotic flow modifying reagent.

Figure 8:
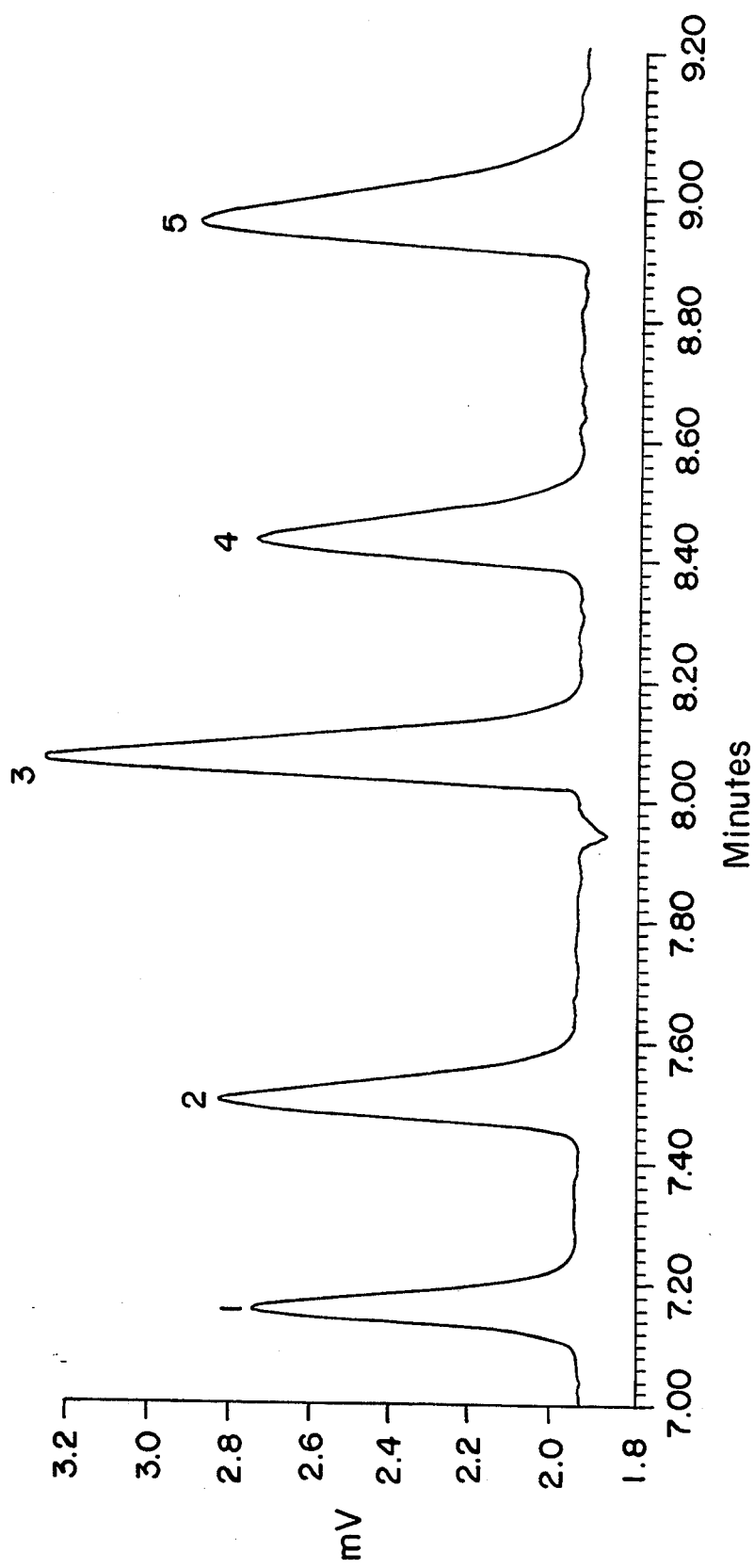
FIG. 8 is an electropherogram obtained by slowing down the electroosmotic flow and shows separation of five anions by CE using chromate as the detection anion and 3-N,N-dimethylpalmitylammonia propanesulfonate as the electroosmotic flow modifying reagent.

The five anions were separated and detected by the procedure in less than ten minutes, as shown in FIG. 8.

The five anions shown in FIG. 8 are:

|   | anions | ppm |
|---|---|---|
| 1. | bromide | 4 |
| 2. | chloride | 2 |
| 3. | sulfate | 4 |
| 4. | nitrite | 4 |
| 5. | nitrate | 4 |

EXAMPLE 11

CE Separation of a Mixture of Seven Anions by Slowed Down Electroosmotic Flow Using Tween 20 as the Electroosmotic Flow Modifying Reagent The separation of a mixture of seven anions by slowed down electroosmotic flow was carried out according to the general procedure and conditions described in Example 9, except that 0.5 mM Tween 20 (polyoxyethylenesorbitan monolaurate) was the electroosmotic flow modifying reagent. Indirect UV/visible detection was carried out at 272 nm.

Figure 9:
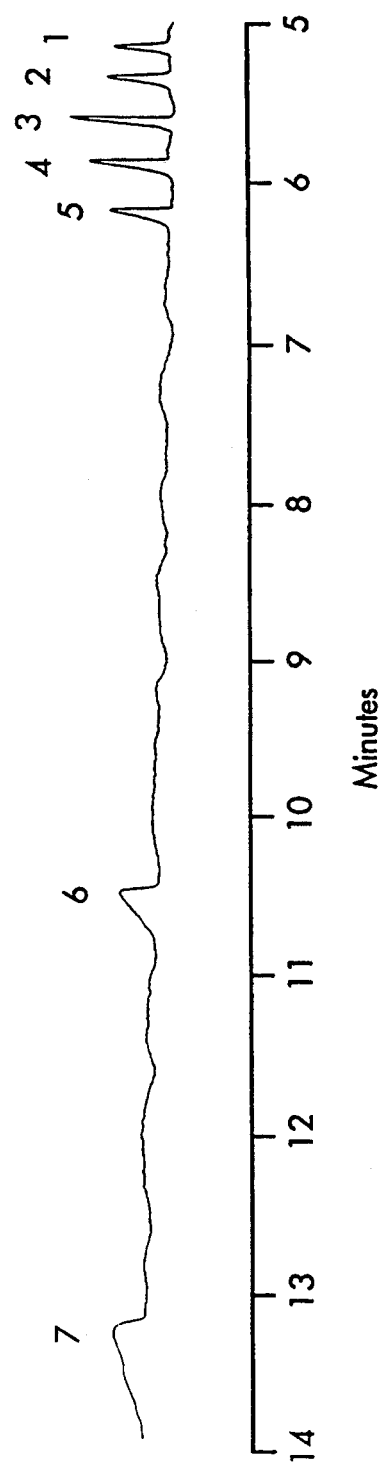
FIG. 9 is an electropherogram obtained by slowing down the electroosmotic flow and shows separation of anions by CE using chromate as the detection anion and Tween 20 as the electroosmotic flow modifying reagent.

The seven anions were separated and detected by the procedure in less than fourteen minutes, as shown in FIG. 9.

The seven anions shown in FIG. 9 are:

|   | anions | ppm |
|---|---|---|
| 1. | bromide | 4 |
| 2. | chloride | 2 |
| 3. | sulfate | 4 |
| 4. | nitrite | 4 |
| 5. | nitrate | 4 |
| 6. | fluoride | 1 |
| 7. | phosphate | 6 |

EXAMPLE 12

CE Separation of a Mixture of Anions by Slowed Down Electroosmotic Flow Using Capillaries with Modified Capillary Walls The separation of a mixture of anions by slowed down electroosmotic flow was carried out according to the general procedure and conditions described in Example 9, except that an electroosmotic flow modifying reagent was not used. Instead, the capillary walls were either coated with a polymeric material or the capillary was constructed of a unique substance.

The capillary wall differences and the separation pattern for the eight anions is shown in FIG. 10. The reference capillary was constructed of fused silica and yielded crowded separation of the anions under the present separation conditions. In contrast, the capillaries whose walls were coated with polyethylene glycol (PEG; FIG. 10a), polymethylsiloxane (PMS; FIG. 10b), polybutadiene maleic acid copolymer (PBDMA; FIG. 10c) and a capillary constructed of a proprietary material of Scientific Glass Engineering (SGE; FIG. 10d) yielded a more separated pattern of anion peaks.

Figure 10A:
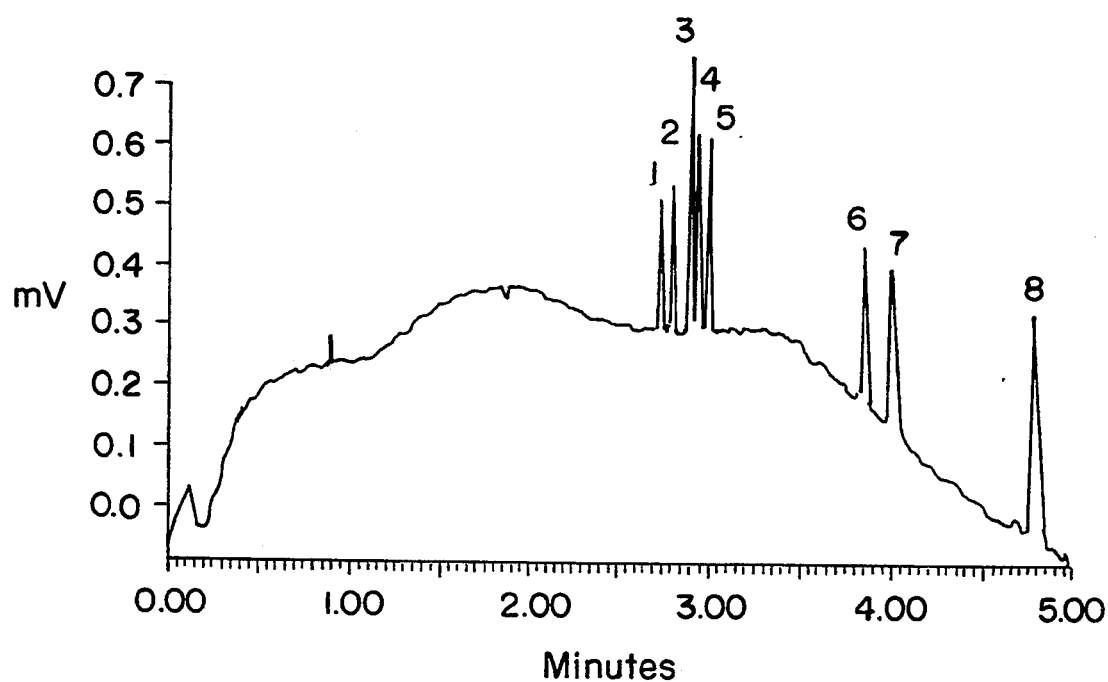
FIG. 10 is a series of chromatograms obtained by slowing down the electroosmotic flow and shows separation of anions by CE using chromate as the detection anion where the inner surface of the capillary is modified by the presence of the following substances:
(a) polyethylene glycol (PEG),
(b) polymethylsiloxane (PMS)
(c) polybutadiene maleic acid copolymer (PBDMA),
(d) proprietary modified capillary of Scientific Glass Engineering (SGE).
Figure 10B:
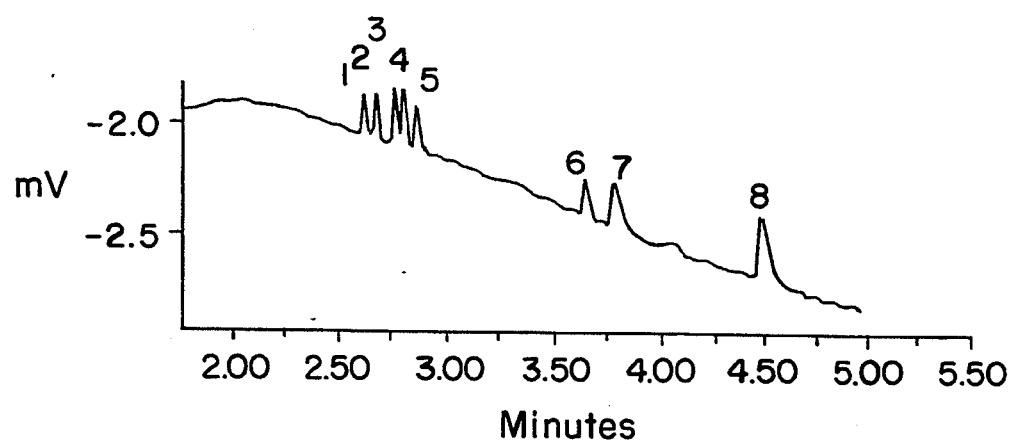

For the anion separations shown in FIGS. 10a and b, the anions shown are:

| | anion | ppm |
|---|---|---|
| 1. | bromide | 4 |
| 2. | chloride | 2 |
| 3. | sulfate | 4 |
| 4. | nitrite | 4 |
| 5. | nitrate | 4 |
| 6. | fluoride | 1 |
| 7. | phosphate | 4 |
| 8. | carbonate | 4 |

Figure 10C:
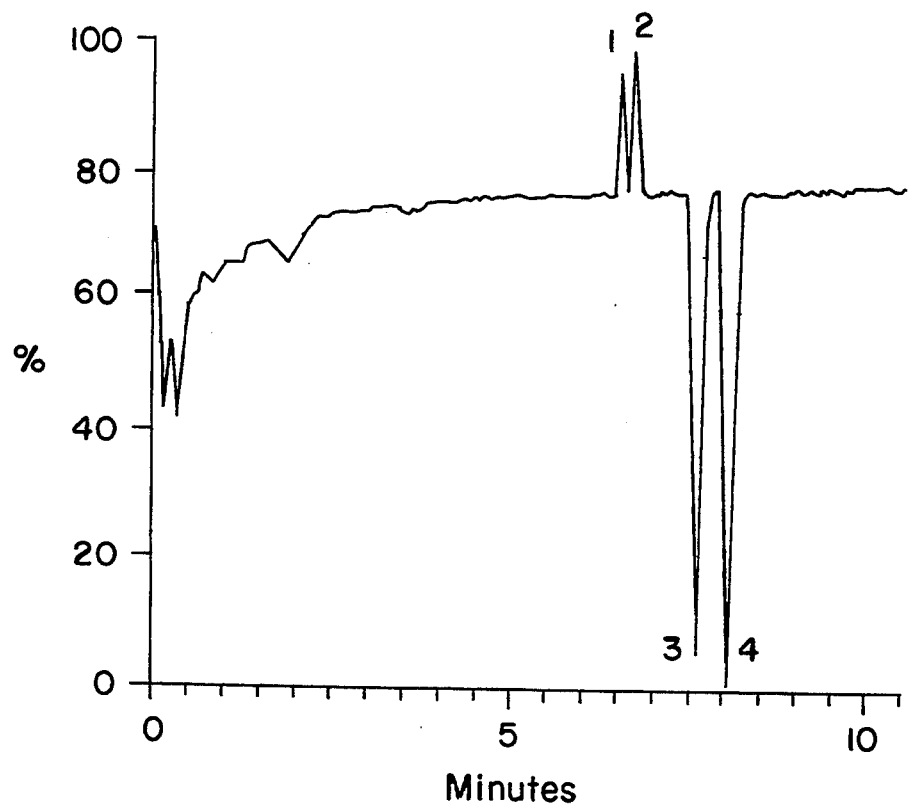
Figure 10D:
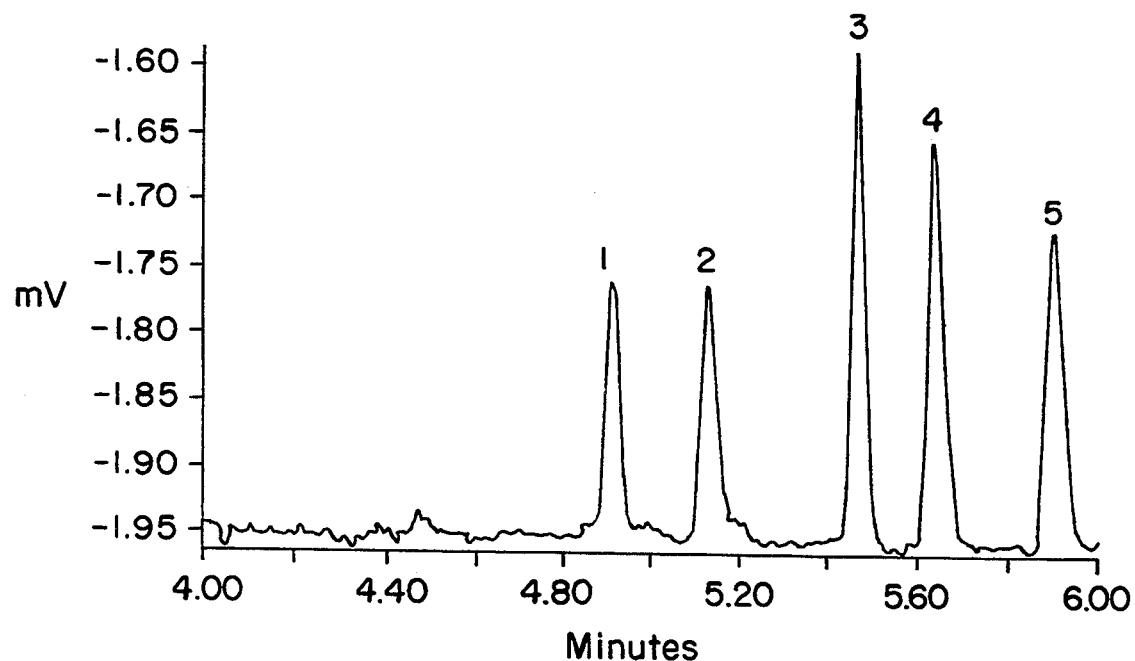

For the anion separations shown in FIG. 10d, the anions shown are:

| | anion | ppm |
|---|---|---|
| 1. | bromide | 4 |
| 2. | chloride | 2 |
| 3. | sulfate | 4 |
| 4. | nitrite | 4 |
| 5. | nitrate | 4 |

For the anion separations shown in FIG. 10c, the anions shown are:

| | anion | ppm |
|---|---|---|
| 1. | chloride | 2 |
| 2. | sulfate | 4 |
| 3. | nitrite | 4 |
| 4. | nitrate | 4 |

The detection anion for the separations shown in FIG. 10c was 5 mM bromide as the potassium salt rather than chromate. Indirect UV/visible detection was carried out at 214 nm.

EXAMPLE 13

CE Separation of a Mixture of Nine Anions Using a Modified Capillary

Figure 11:
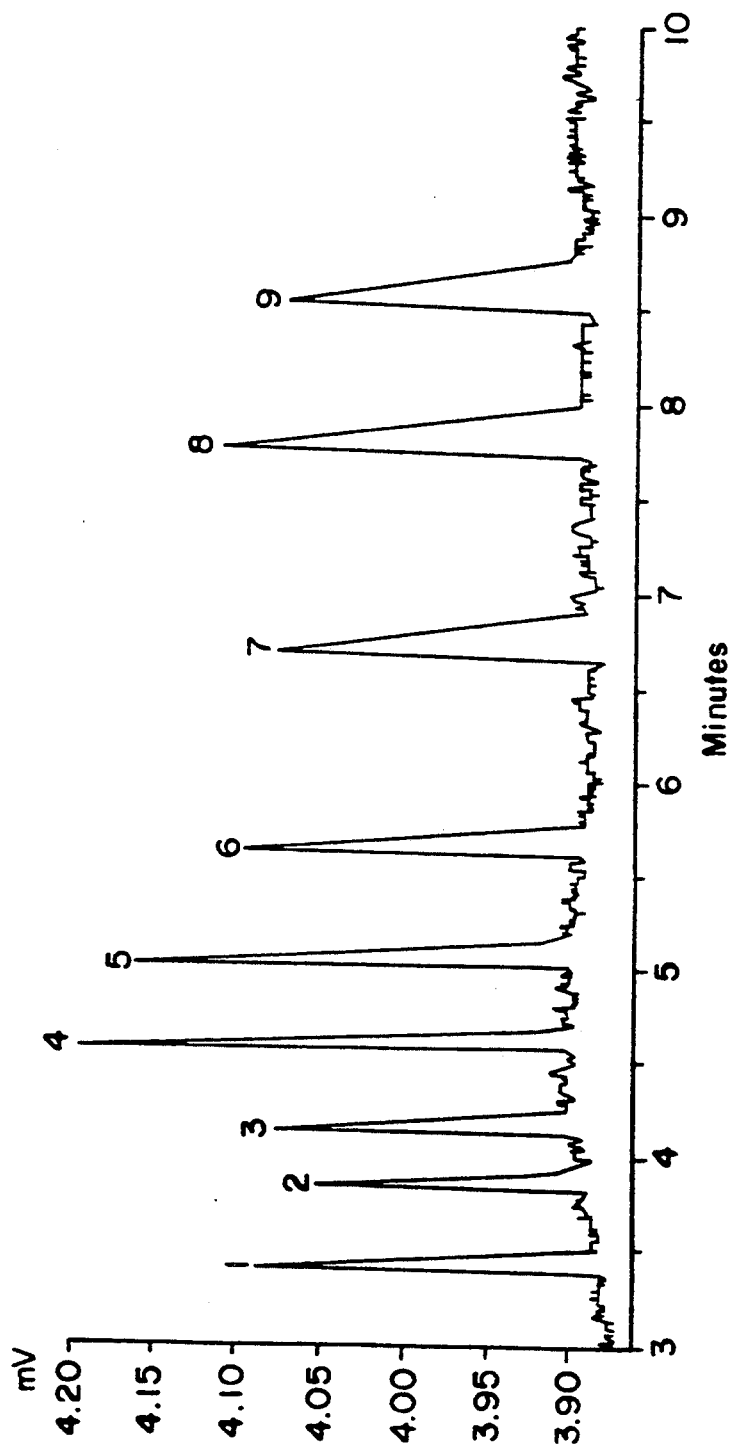
FIG. 11 is an electropherogram showing the separation of nine anions by CE using $Na_2CrO_4$ as the carrier electrolyte and modifying the capillary walls with an uncharged polymer, effectively shielding the silanol groups on the walls.

The separation of a mixture of nine anions was carried out according to the procedure described in Example 9, except that no flow modifier (TTAB) was used. The capillary wall was modified by covering the inner wall with a layer of PSDVB polymer to shield the negative charges of the silanol groups present on the wall. The capillary was 46 cm in length and had an internal diameter of 50 $\mu$m. All nine anions were separated by the procedure in less than nine minutes, as shown in FIG. 11. The anions shown in FIG. 11 are:
1. thiosulfate
2. bromide
3. chloride
4. sulfate
5. nitrite
6. nitrate
7. molybdate
8. azide
9. tungstate.

EXAMPLE 14

CE Separation of Five Anions Using an Amphoteric Flow Modifier

Separation of a mixture of five anions was carried out according to the procedure described in Example 9, except that an amphoteric detergent, 3(N,N-dimethylpalmitylammonio)propanesulfonate (pH 8, 0.5 mM), was used. The capillary was 60 cm in length and had an internal diameter of 75 $\mu$m. All five anions were separated in about nine minutes, as shown in FIG. 12.

Figure 12:
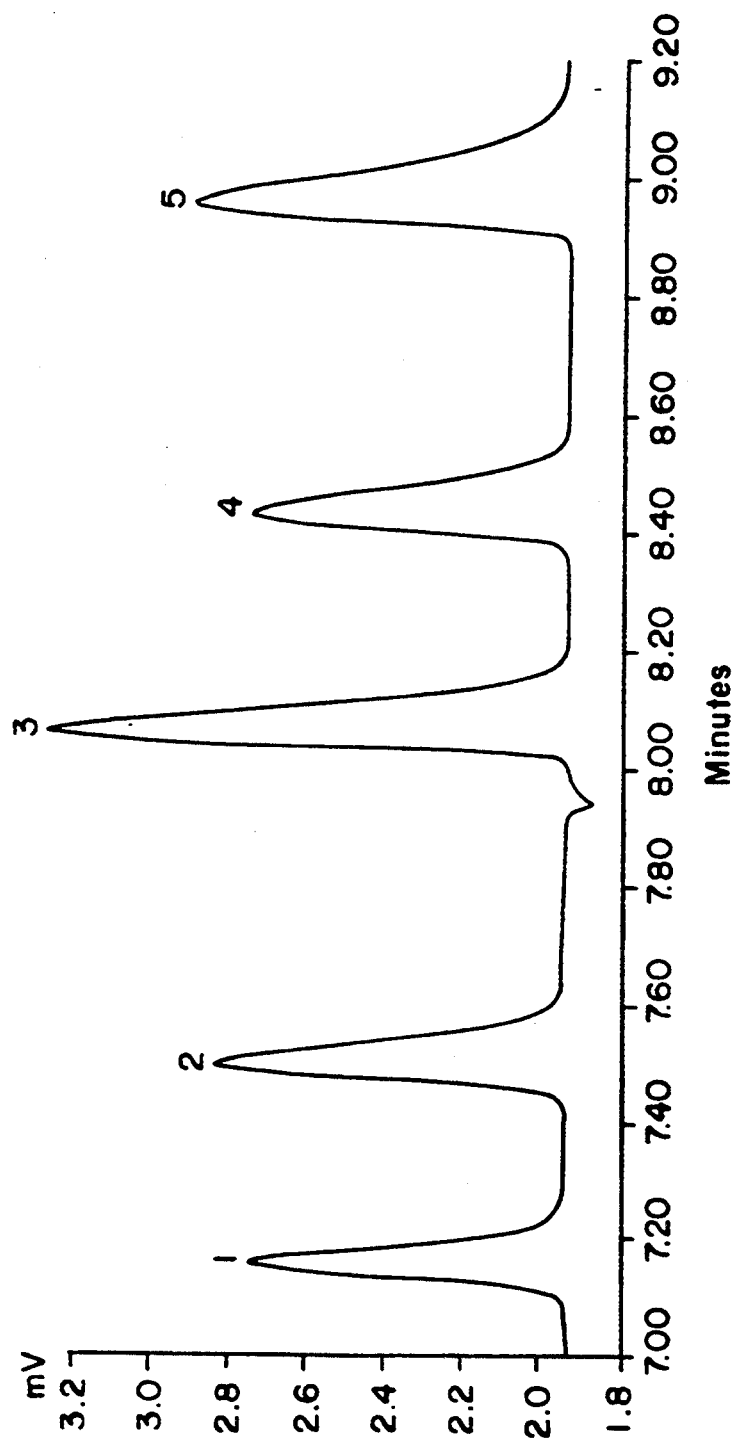
FIG. 12 is an electropherogram showing the separation of five anions by CE using $Na_2CrO_4$ and an amphoteric flow modifier as the carrier electrolyte.

The anions shown in FIG. 12 are:
1. Br
2. Cl
3. $SO_4$
4. $NO_2$
5. $NO_3$

EXAMPLE 15

Figure 13:
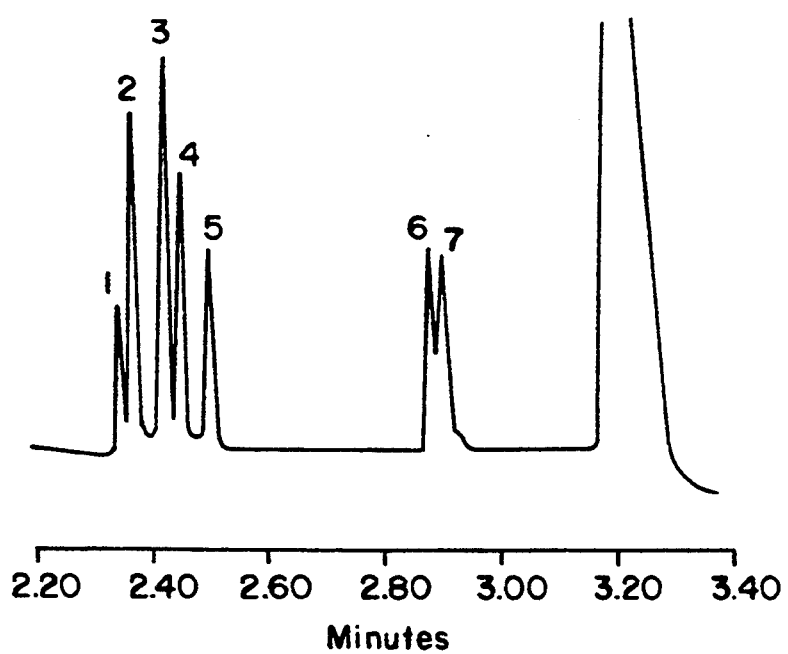
FIG. 13 is an electropherogram showing the separation of eight anions by CE using TTAB/$Na_2CrO_4$ and octanesulfonate as an electromigrative agent.

Improving Sensitivity of Separation of an Eight Anion Mixture by Electromigrative Sample Introduction CE separation of an eight anion mixture was carried out as described in Example 1 above, except that an electromigration enhancer sodium octanesulfonate, was added to enhance sensitivity for trace amounts of anions. The carrier electrolyte contained 5 mM chromate and 0.5 mM TTAB electroosmotic flow modifier and was adjusted to pH 8.1. Fused silica capillary (75 $\mu$m internal diameter, 52 cm from the point of sample introduction to the detector) was used for the separation. During the analysis, the injection side was at $-20$ kV. The electromigrative sample introduction was carried out at 5 kV for 45 seconds. Sample conductivity was adjusted by the addition of sodium octanesulfonate at 18 $\mu$N to the sample. The peak identities, ppb concentrations and nM detection limits (3× the noise), shown in FIG. 13, were as follows: Peak 1: Bromide 4 ppb, 13.6 nM; 2: Chloride 4 ppb, 13 nM; 3: Sulfate 4 ppb, 8.4 nM, 4: Nitrite 4 ppb, 25.4 nM; 5: Nitrate 4 ppb, 24 nM; 6: Fluoride 2 ppb, 19.8 nM and 7-Phosphate 8 ppb 17.8 nM. The large peak at about 3.2 minutes is the carbonate. The levels of carbonate were not controlled under the conditions of this experiment. These results show that the detection limits (calculated as 3× noise in concentration units) for this separation are in the low nanomolar range, which represents at least a hundred-fold increase in sensitivity in comparison with the results achievable in the same carrier electrolyte without the addition of sodium octanesulfonate to the sample.

EXAMPLE 16

Separation of a Thirty Anion Mixture Using Electromigrative Sample Introduction

Figure 14:
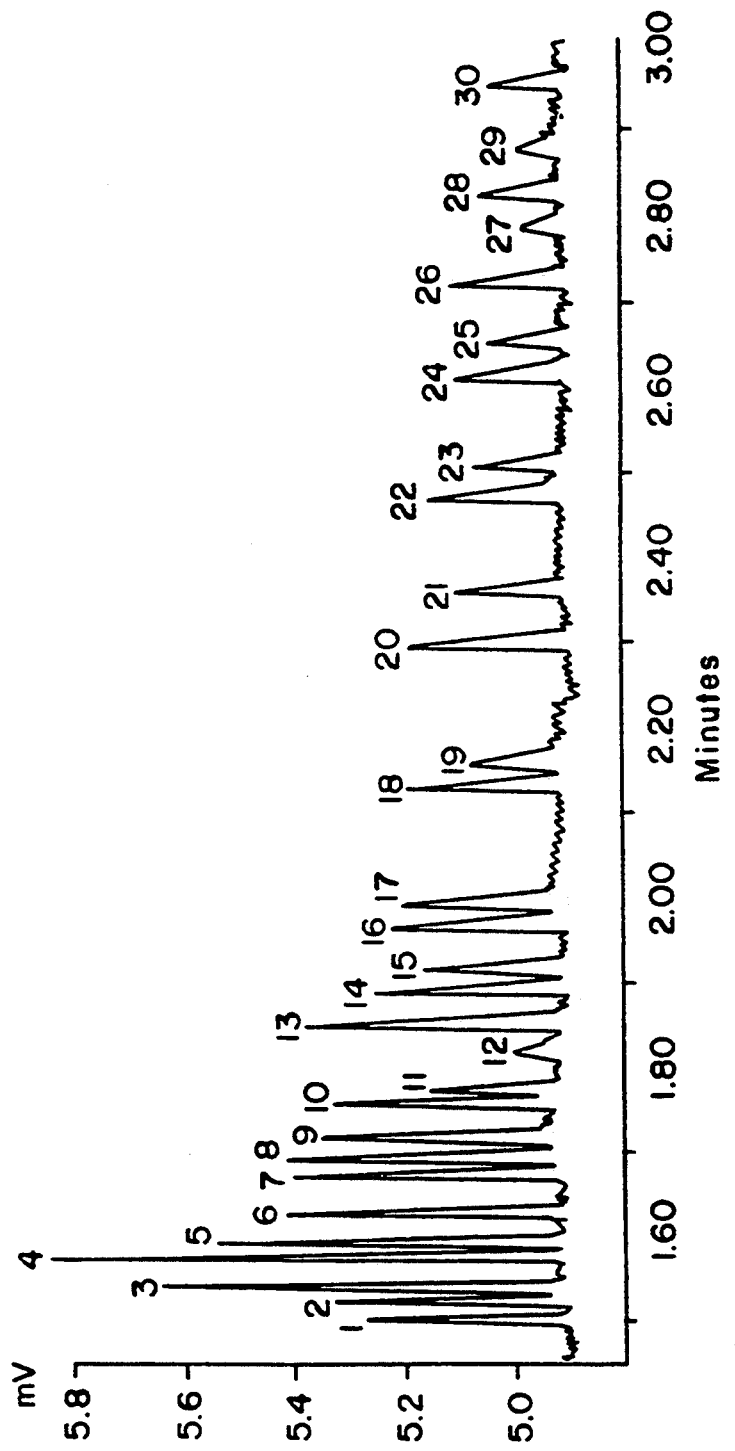
FIG. 14 is an electropherogram showing the separation of thirty anions by CE using TTAB/$Na_2CrO_4$ and electromigrative sample injection.

CE separation of a thirty anion mixture was carried out as described in Example 15, using electromigrative sample introduction except that no sodium octanesulfonate was used. The electromigrative sample introduction was carried out at 1 KV for 14 seconds. The capillary was 60 cm in length and had an internal diameter of 50 $\mu$m. The electrolyte was 5 mM $Na_2CrO_4$ and 0.5 mM TTAB, pH 8.0. All thirty anions were separated in less than three minutes, as shown in FIG. 14. The anions shown in FIG. 14 are listed below:
1. thiosulfate 2. bromide
3. chloride
4. sulfate
5. nitrite
6. nitrate
7. molybdate
8. azide
9. tungstate
10. monofluorophosphate
11. chlorate
12. citrate
13. fluoride
14. formate
15. phosphate
16. phosphite
17. chlorite
18. galactarate
19. carbonate
20. acetate
21. ethanesulfonate
22. propionate
23. propanesulfonate
24. butyrate
25. butanesulfonate
26. valerate
27. benzoate
28. glutamate
29. pentanesulfonate
30. gluconate

EQUIVALENTS

Those skilled in the art will recognize, or be able to ascertain using no more than routine experimentation, equivalents to the specific embodiments of the invention described specifically herein. Such equivalents are intended to be encompassed in the scope of the following claims.

We claim:

1. A method for detecting anions in a sample using capillary zone electrophoresis comprising the steps of:
   a) introducing the sample into a capillary;
   b) immersing the capillary in a carrier electrolyte containing a salt selected from the group consisting of molybdate, tungstate, ferrocyanide, ferricyanide, bromide, iodide and dichromate;
   c) applying an electrical current under conditions appropriate for the anions in the sample to move along the capillary toward the detection electrode, thereby causing separation of the anions to occur; and
   d) detecting the anions indirectly using a UV/visible photometric detector.

2. The method of claim 1 wherein the salt is a sodium salt having a concentration of from about 1.0 mM to about 20 mM.

3. The method of claim 1 wherein electrical voltage is from about 5 KV to about 40 KV.

4. The method of claim 1 wherein an electromigration additive is added to the sample.

5. The method of claim 4 wherein the electromigration additive is selected from the group consisting of an octanesulfonate salt, a carbonate salt and a citrate salt.

6. The method of claim 1 wherein the carrier electrolyte additionally contains an electroosmotic flow modifier.

7. The method of claim 6 wherein the electroosmotic flow modifier is selected from the group consisting of a cellulose, a glycol, a surfactant and a polyacrylamide.

8. The method of claim 7 wherein the electroosmotic flow modifier is selected from the group consisting of methylcellulose, hydroxypropylmethylcellulose and Tween 20.

9. The method of claim 6 wherein the electroosmotic flow modifier is selected from the group consisting of guanidine, diaminononane, di-n-butylamine and 3-N,N-dimethylpalmitylammonia propanesulfonate.

10. The method of claim 1 wherein the capillary has an electroosmotic flow modification to the capillary inner surface.

11. The method of claim 10 wherein the electroosmotic flow modification is a coating of the capillary inner surface with a substance selected from the group consisting of polyethylene glycol, polymethylsiloxane and polybutadiene maleic acid copolymer.

12. A method for detecting anions in a sample using capillary zone electrophoresis comprising the steps of:
   a) introducing the sample into a capillary;
   b) immersing the capillary in a carrier electrolyte containing a chromate or vanadate salt and an electroosmotic flow modifier selected from the group consisting of a cellulose, a glycol, a surfactant, a polyacrylamide, guanidine, diaminononane, di-n-butylamine and 3-N,N-dimethylpalmitylammonia propanesulfonate;
   c) applying an electrical current under conditions appropriate for the anions in the sample to move along the capillary toward the detection electrode, thereby causing separation of the anions to occur; and
   d) detecting the anions indirectly using a UV/visible photometric detector.

13. A method for detecting anions in a sample using capillary zone electrophoresis comprising the steps of:
   a) introducing the sample into a capillary whose inner surface is coated with a substance selected from the group consisting of polyethylene glycol, polymethylsiloxane and polybutadiene maleic acid copolymer;
   b) immersing the capillary in a carrier electrolyte containing a chromate or vanadate salt;
   c) applying an electrical current under conditions appropriate for the anions in the sample to move along the capillary toward the detection electrode, thereby causing separation of the anions to occur; and
   d) detecting the anions indirectly using a UV/visible photometric detector.

* * * * *